United States Patent [19]

Jean

[11] Patent Number: 5,169,394
[45] Date of Patent: Dec. 8, 1992

[54] FEMININE SANITARY NAPKIN

[76] Inventor: Lai D. Jean, No. 72, Chengfang Rd., Taliao Hsiang, Kaohsiung Hsien, Taiwan

[21] Appl. No.: 750,252

[22] Filed: Aug. 27, 1991

[51] Int. Cl.⁵ .............................................. A61F 3/20
[52] U.S. Cl. ................................. 604/385.1; 604/397
[58] Field of Search ................. 604/378, 385.1, 385.2, 604/397, 398

[56] References Cited

U.S. PATENT DOCUMENTS

| | | | |
|---|---|---|---|
| 3,183,909 | 5/1965 | Roehr | 604/385.1 |
| 4,031,897 | 6/1977 | Graetz | 604/385.2 X |
| 4,743,245 | 5/1988 | Lassen et al. | 604/385.1 |
| 4,781,713 | 11/1988 | Welch et al. | 604/385.1 |
| 4,950,263 | 8/1990 | Lewis | 604/385.1 |

FOREIGN PATENT DOCUMENTS 9014063  11/1990  World Int. Prop. O. ......... 604/378

Primary Examiner—Randall L. Green
Assistant Examiner—D. Willse
Attorney, Agent, or Firm—Bacon & Thomas

[57] ABSTRACT

A feminine sanitary napkin employs two absorption devices: a primary absorbing device and a secondary absorbing device, both absorbing devices being made out of at least one layer of absorbent material for absorbing menses. The primary absorbing device is generally tubular and hollow; is received within the secondary absorbing device, which is substantially conventionally shaped; and is fixed by means of a transfer element in the form of a stem to a position slightly below an outside surface of the secondary absorbing device, thereby extending perpendicularly therefrom.

10 Claims, 4 Drawing Sheets

FEMININE SANITARY NAPKIN

BACKGROUND OF THE INVENTION

The present invention relates to feminine sanitary napkins.

Conventional sanitary napkins comprise at least one layer of absorbent material, one side of which is directed toward the body and the other side, customarily with an adhesive strip, is placed against the undergarment.

A disadvantage of conventional sanitary napkins is the non-adaptable nature thereof. The anatomical variation of the female human body is great. Conventional napkins are designed for the average; therefore, they may not always fit every user comfortably.

Therefore, there has been a long and unfulfilled need in the related art for a feminine sanitary napkin which accommodates the physical differences between individual users.

SUMMARY OF THE INVENTION

The present invention provides a feminine sanitary napkin which employs two absorption devices: a primary absorbing means and a secondary absorbing means, both absorbing means being made out of at least one layer of absorbent material for absorbing menses. The primary absorbing means is generally tubular and hollow; is received within the secondary absorbing means, which is substantially conventionally shaped; and is fixed by means of a transfer means made of absorbent material to a position slightly below an outside surface of the secondary absorbing means, thereby extending in a curved fashion perpendicularly therefrom.

The primary absorbing means is positioned at the vestibule of the vagina between the labia minora while the secondary absorbing means covers the vulva. The primary absorbing means is extendible from the secondary absorbing means under the influence of the user, thereby being adjustable to accommodate anatomical variations of different users. The primary absorbing means is anchorable in an extended position from the secondary absorbing means by means of the coefficients of friction of the respective contacting surfaces thereof.

Advantages and features of novelty which characterize the invention are pointed out with particularity in the claims annexed hereto and forming a part hereof. However, for a better understanding of the invention, reference should be made to the accompanying drawings in relation to the detailed description hereunder.

DETAILED DESCRIPTION OF THE PREFERRED EMBODIMENTS

Figure 1:
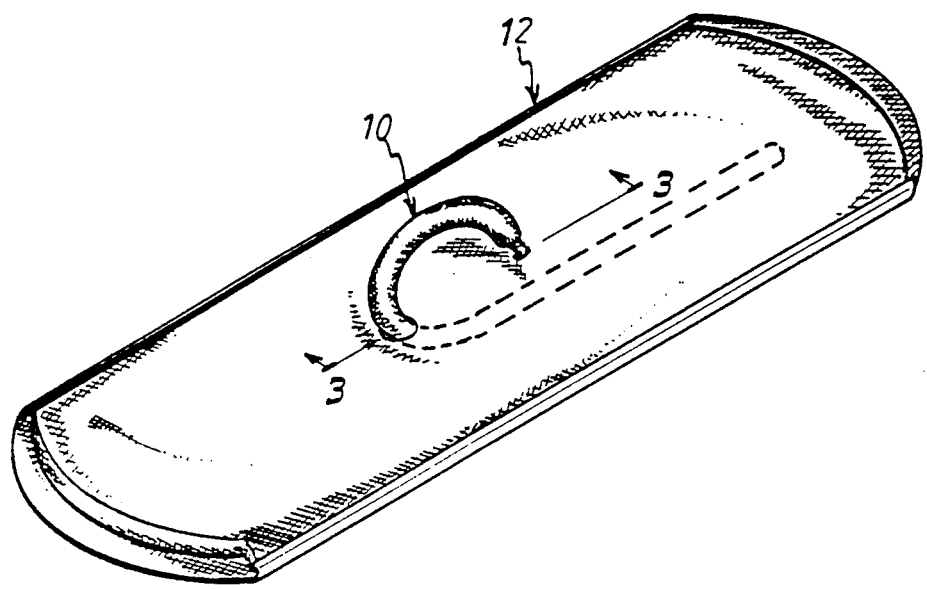
FIG. 1 is a perspective view of a feminine sanitary napkin shown in a preferred embodiment in accordance with the present invention.
Figure 2:
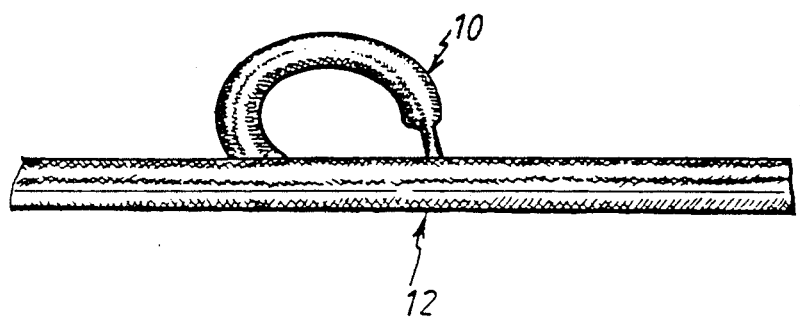
FIG. 2 is a side view of a preferred embodiment of the sanitary napkin.

Now referring to the drawings, initially to FIGS. 1 and 2, a preferred embodiment in accordance with the present invention of a feminine sanitary napkin is shown and generally comprises a primary absorbing means 10 and a secondary absorbing means 12. In general, both absorbing means 10 and 12 are made of an absorbent material, with the primary absorbing means 10 being tubularly shaped and the secondary absorbing means 12 being substantially conventionally shaped. The primary absorbing means 10 is slidably received in the secondary absorbing means 12 and extends therefrom in a perpendicular relationship thereto. It should be known that the secondary absorbing means 12 has an impermeable layer on a second side thereof which is placed against an undergarment and prevents menses from being absorbed thereby.

Figure 3:
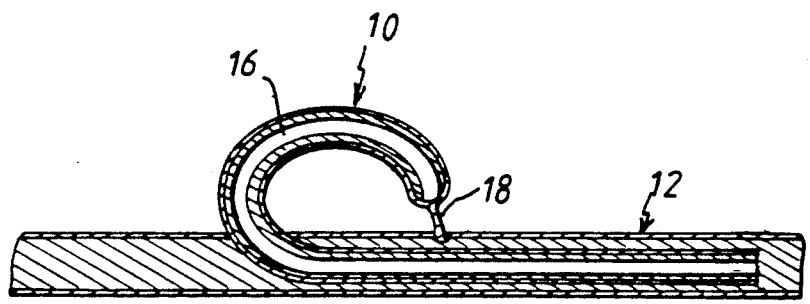
FIG. 3 is a cross-sectional view taken at line 3—3 of FIG. 1, showing a primary absorbing means in a retracted position.

The present invention is shown in more detail in FIG. 3. The primary absorbing means 10 has an inner passage 16 formed therein. The inner passage 16 is open at an inner end thereof, an end received within the secondary absorbing means 12, while an outer end thereof leads into a transfer means 18 made of absorbent material. The transfer means 18 is fixed to and serves as a bridge between the primary absorbing means 10 and the secondary absorbing means 12, being fixed to the latter slightly below the surface thereof at a point substantially in longitudinal line with a portion of the primary absorbing means 10 that is received within the secondary absorbing means 12. As can be seen, the primary absorbing means 10 curves back toward itself to be fixed to the secondary absorbing means 12, the transfer means 18 serving as a pivot therebetween.

Figure 4:
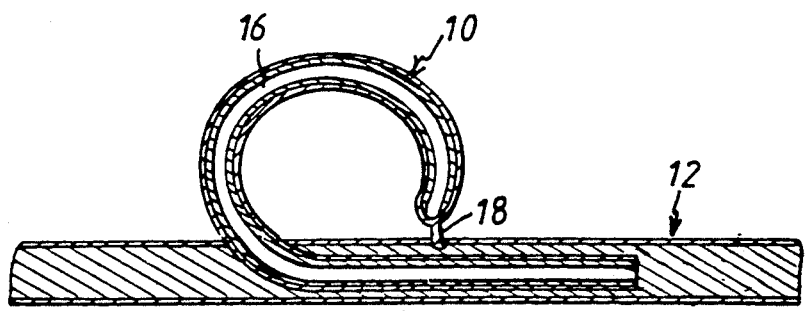
FIG. 4 is a view similar to FIG. 3, showing the primary absorbing means in an extended position.

With additional reference to FIG. 4, the primary absorption means 10 is extendible from an innermost position, as shown in FIG. 3, to an extended position, as shown in FIG. 4, which is accomplished under the influence of a user simply by pulling the primary absorbing means 10 between the thumb and a finger. The primary absorbing means 10 is anchorable in an extended position from the secondary absorbing means 12 by means of the coefficients of friction of the respective contacting surfaces thereof.

Figure 5:
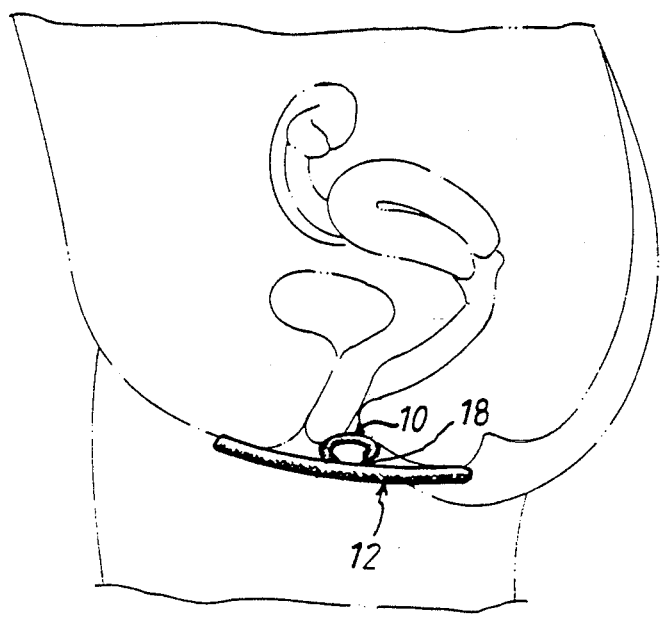
FIG. 5 is a side plan view of the sanitary napkin in relation to the genitourinary anatomy of a female human body.

Now referring to FIG. 5, the function of both absorbing means 10 and 12 is for absorbing menses, with the primary absorbing means 10 having the further function of transferring menses to the secondary absorbing means 12. From the longitudinal configuration of the primary absorbing means 10 being fixed to and received by the secondary absorbing means 12 (cf. FIGS. 1 and 2), the primary absorbing means 10 extends to the vestibule of the vagina, between the labia minora, with the secondary absorbing means 12 covering the vulva in a conventional manner. Depending on the size of the vulva, the primary absorbing means 10 can be extended (or retracted) to be properly placed at the vestibule of the vagina.

When the sanitary napkin of the present invention is in place, the primary absorbing means 10 absorbs menses initially, with the menses being absorbed through to the inner passage 16. Thereafter, the menses flow to the portion of the primary absorbing means 10 positioned in the secondary absorbing means 12, and are subsequently absorbed into the secondary absorbing means 12 or the auxiliary absorbing means 20, if need be, either through the absorbent material thereof or from the inner end of the primary absorbing means 10. From the inner passage 16, menses can also flow through the transfer means 18 into the secondary absorbing means 12.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

I claim:

1. A feminine sanitary napkin, comprising a primary absorbing means for absorbing menses and a secondary absorbing means for absorbing menses, said primary absorbing means being attached to said secondary absorbing means and extendible between the labia minora to the vestibule of the vagina, said secondary absorbing means adapted to cover the vulva wherein said primary absorbing means comprises an elongated absorbing member having a first end portion attached to the secondary absorbing means and a second end portion slidably attached to the secondary absorbing means so as to enable the relative positions of the primary and secondary absorbing means to be adjusted by sliding the second end portion of the elongated absorbing member relative to the secondary absorbing means.

2. A sanitary napkin as claimed in claim 1, wherein said elongated absorbing member is extendible from the secondary absorbing means.

3. A sanitary napkin as claimed in claim 1, wherein said secondary absorbing means comprises a front side and a back side, said front side for being placed against the body and said back side for being placed against the undergarment, said backside comprising an impermeable layer.

4. A sanitary napkin as claimed in claim 3, wherein said elongated absorbing member is generally cylindrically shaped and said secondary absorbing means longitudinally receives the second end portion of said elongated absorbing member, said elongated absorbing member being fixedly attached at the first end portion thereof to said front side of said secondary absorbing means, said elongated absorbing member being manually extendible from and anchorable in said secondary absorbing means.

5. A sanitary napkin as claimed in claim 4, wherein said elongated absorbing member defines an inner passage formed therein extending from a first end thereof to a second end thereof.

6. A sanitary napkin as claimed in claim 5, wherein said inner passage of said elongated absorbing member is open at said second end thereof.

7. A sanitary napkin as claimed in claim 5, further comprising a transfer means for transferring menses from said elongated absorbing member to said secondary absorbing means.

8. A sanitary napkin as claimed in claim 7, wherein said transfer means comprises an absorbent material.

9. A sanitary napkin as claimed in claim 7, wherein said transfer means is fixed to said first end of said elongated absorbing member and is fixed to said first side of said secondary means.

10. A sanitary napkin as claimed in claim 7, wherein said transfer means is fixed to said first end of said elongated absorbing member and is fixed to said first side of said secondary means at a point located slightly below an outside surface thereof and aligned with said second end portion of said elongated absorbing member slidably received in said secondary absorbing means.

* * * * *